(12) United States Patent
Malic et al.

(10) Patent No.: US 9,291,567 B2
(45) Date of Patent: Mar. 22, 2016

(54) MICROFLUIDIC SYSTEM HAVING MONOLITHIC NANOPLASMONIC STRUCTURES

(76) Inventors: Lidija Malic, Montreal (CA); Keith Morton, Saint Bruno (CA); Teodor Veres, Montreal (CA)

( * ) Notice: Subject to any disclaimer, the term of this patent is extended or adjusted under 35 U.S.C. 154(b) by 64 days.

(21) Appl. No.: 14/005,347

(22) PCT Filed: Mar. 12, 2012

(86) PCT No.: PCT/CA2012/000203
§ 371 (c)(1),
(2), (4) Date: Sep. 16, 2013

(87) PCT Pub. No.: WO2012/122628
PCT Pub. Date: Sep. 20, 2012

(65) Prior Publication Data
US 2014/0004507 A1    Jan. 2, 2014

Related U.S. Application Data

(60) Provisional application No. 61/452,868, filed on Mar. 15, 2011.

(51) Int. Cl.
*G01N 1/30* (2006.01)
*G01N 21/65* (2006.01)
(Continued)

(52) U.S. Cl.
CPC ........ *G01N 21/658* (2013.01); *B01L 3/502707* (2013.01); *B01L 3/502715* (2013.01);
(Continued)

(58) Field of Classification Search
None
See application file for complete search history.

(56) References Cited

U.S. PATENT DOCUMENTS

| 5,725,788 A | 3/1998 | Maracas et al. |
| 6,686,184 B1 | 2/2004 | Anderson et al. |

(Continued)

FOREIGN PATENT DOCUMENTS

| CA | 2710828 | 7/2009 |
| CN | 101571536 | 11/2009 |

(Continued)

OTHER PUBLICATIONS

Balasundaram G et al, Increased osteoblast adhesion on nanograined Ti modified with KRSR, (2007) J. Biomed. Mater. Res., Part A. 80a, 602-611.

(Continued)

*Primary Examiner* — Robert T Crow
(74) *Attorney, Agent, or Firm* — Jason E.J. Davis (57) ABSTRACT

A microfluidic system has a monolithic biocompatible substrate with both a surface having an ordered array of nano-scale elements for plasmonic response monitoring and a network of microchannels. Advantageously, low-volume consumption, rapid low-cost fabrication of molds with easily interchangeable microfluidic channel layouts, mass production, and in situ label-free real-time detection of cellular response, viability, behavior and biomolecular binding using plasmonic techniques can be provided. A ratio of greater than 0.2 of the cross-sectional dimension and the spacing between the nano-scale elements is useful for plasmonic response monitoring. Producing such a system involves a master mold with the nano-scale elements etched into a hard substrate, and the network provided in a soft membrane bonded to the hard substrate. A stamp may be created by setting a settable liquid polymer or metal placed in the master mold. Features of the intended device can be transferred to a polymeric substrate using the stamp.

24 Claims, 4 Drawing Sheets

(51) Int. Cl.
 B82Y 30/00 (2011.01)
 C12M 3/06 (2006.01)
 G01N 21/552 (2014.01)
 B01L 3/00 (2006.01)
(52) U.S. Cl.
 CPC .............. *B82Y30/00* (2013.01); *C12M 23/16* (2013.01); *G01N 21/554* (2013.01); *B01L 2300/0654* (2013.01); *B01L 2300/0822* (2013.01); *B01L 2300/0896* (2013.01); *B01L 2400/086* (2013.01); *Y10T 137/8593* (2015.04)

(56) References Cited

U.S. PATENT DOCUMENTS

| | | | |
|---|---|---|---|
| 6,808,646 | B1 | 10/2004 | Jeans |
| 6,864,480 | B2 | 3/2005 | Staats |
| 6,923,216 | B2 | 8/2005 | Extrand et al. |
| 7,295,320 | B2 | 11/2007 | Ostlin et al. |
| 7,323,143 | B2 | 1/2008 | Anderson et al. |
| 7,473,090 | B2 | 1/2009 | McMackin et al. |
| 7,557,051 | B2 | 7/2009 | Ryu et al. |
| 7,704,322 | B2 | 4/2010 | Hansen et al. |
| 7,758,794 | B2 | 7/2010 | Chou et al. |
| 7,766,055 | B2 | 8/2010 | Unger et al. |
| 7,820,270 | B2 | 10/2010 | Black et al. |
| 2005/0170670 | A1 | 8/2005 | King et al. |
| 2006/0205092 | A1 | 9/2006 | Lackritz et al. |
| 2007/0015288 | A1 | 1/2007 | Hulteen et al. |
| 2008/0105565 | A1* | 5/2008 | Davalos et al. ............ 205/775 |
| 2009/0061152 | A1 | 3/2009 | DeSimone et al. |
| 2009/0250130 | A1 | 10/2009 | Studer et al. |
| 2010/0003666 | A1 | 1/2010 | Lee et al. |
| 2012/0028342 | A1 | 2/2012 | Ismagilov et al. |

FOREIGN PATENT DOCUMENTS

| | | |
|---|---|---|
| CN | 101629143 | 1/2010 |
| EP | 0257955 | 3/1988 |
| EP | 2042467 | 4/2009 |
| WO | WO2004089546 | 10/2004 |
| WO | WO2008097360 | 8/2008 |
| WO | 2009022985 | 2/2009 |
| WO | WO2009064816 | 5/2009 |
| WO | WO2011106057 | 9/2011 |

OTHER PUBLICATIONS

Barbucci R, et al, Micro and nano-structured surfaces, (2003) J. Mater. Sci. 14, 721-725.
Bedner et al., Enzyme kinetic reactions and fluorochrome uptake rates measured in individual cells by laser scanning cytometry (LSC) (1998) Cytometry. 33, 1-9.
Blummel J, et al, Protein repellent properties of covalently attached PEG coatings on nanostructured SiO2-based interfaces, (2007) Biomaterials. 28, 4739-4747.
Cavalcanti-Adam, Ea, et al, Cell spreading and focal adhesion dynamics are regulated by spacing of intergrin ligands, (2007) Biophysical Journal 92, 2964-2974.
Cavalcanti-Adam, Ea et al, Cell adhesion and response to synthetic nanopatterned environments by steering receptor clustering and spatial location (2008) HFSP Journal 2, 276-285.
Curran Jm et al, Introducing dip pen nanolithography as a tool for controlling stem cell behavior: unlocking the potential of the next generation of smart materials in regenerative medicine, (2010) Lab on a Chip. 10, 1662-1670.
Curtis As et al, Nanoimprinting onto cells (2006) J. R. Soc. Interface. 3, 393-398.
Dalby Mj et al, The control of human mesenchymal cell differentiation using nanoscale symmetry and disorder, (2007a) Nat. Mater. 6, 997-1003.
Dalby Mj, et al, Nanotopographical stimulation of mechanotransduction and changes in interphase centromere positioning (2007b) J. Cell. Biochem. 100, 326-338.

Dalby Mj et al, Nanotopographical control of human osteoprogenitor differentiation (2007c) Curr. Stem Cell Res. Ther. 2, 129-138.
Dalby Mj et al, Genomic expression of mesenchymal stem cells to altered nanoscale topographies (2008) J. R. Soc. Interface. 5, 1055-1065.
Dalby Mj, Nanostructured surfaces: cell engineering and cell biology (2009) Nanomedicine. 4, 247-248.
Ernsting Mj, et al, Human monocyte adhesion onto RGD and PHSRN peptides delivered to the surface of a polycarbonate polyurethane using bioactive fluorinated surface modifiers (2007) J. Biomed. Mater. Res., Part A. 83a, 759-769.
Fay, Shawn et al, Real-time analysis of the assembly of ligand, receptor, and G protein by quantitative fluorescence flow cytometry (1991) Biochemistry. 30, 5066-5075.
Griffin et al, Neutrophil elastase up-regulates human β-defensin-2 expression in human brochial epithelial cells. (2003) Febs Letters. 546, 233-236.
Hochbaum A, et al, Bacteria pattern spontaneously on periodic nanostructure arrays (2010) Nanoletters. DOI:10.1021/nl1022290k, pp. 3717-3721.
Kimura K, et al, Stimulation of corneal epithelia migration by a synthetic peptide (PHSRN) corresponding to the second cell-binding site of fibronectin, 2007, Invest. Ophthalmol. Visual Sci. 48, 1110-1118.
Krutzik, Peter, et al, Fluorescent cell barcoding in flow cytometry allows high-throughput drug screening and signaling profiling, (2006) Nature Methods. 3, 361-368.
Lee Lj, et al, Microfluidic enzyme-linked immunosorbent assay technology, (2006) Advances in Clinical Chemistry. (Elsevier) pp. 255-295.
Lim Ct et al, Bead-based microfluidic immunoassays: the next generation (2007) Biosensors and Bioelectronics. 22, 1197-1204.
Malic L, et al, Current state of intellectual property in microfluidic nucleic acid analysis (2007) Recent Patents on Engineering. 1, 71-88.
Marquette C, et al, State of the art and recent advances in immunoanalytical systems (2006) Biosensors and Bioelectronics. 21, 1424-1433.
Myers Frank B., et al, Innovations in optical microfluidic technologies for point-of-care diagnostics (2008) Lab on a Chip. 8, 2015-2031.
Nolan J.P., et al. The emergence of flow cytometry for sensitive, real-time measurements of molecular interactions (1998) Nature Biotechnology. 16, 633-638.
Regehr Kj, et al. Biological implications of polydimethylsiloxane-based microfluidic cell culture (2009) Lab Chip. 9, 2132-2139.
Salber, J et al, Influence of different ECM mimetic peptide sequences embedded in a nonfouling environment on the specific adhesion of human skin keratinocytes and fibroblasts on deformable substrates (2007) Small. 3, 1023-1031.
Weigl, B. et al. Towards non- and minimally instrumented, microfluidics-based diagnostic devices (2008) Lab on a Chip. 8, 1999-2014.
Zhang Y. et al., Microfluidic DNA amplification—A review (2009a) Analytica Chimica Acta. 638, 115-125.
Zhang, C. et al., Micropumps, microvalves, and micromixers within PCR microfluidic chips: advances and trends, 2007 Biotechnology Advances. 25, 483-514.
ISR/WO for corresponding PCT Application No. PCT/CA2012/000203, mailed May 31, 2012.
International Preliminary Report on Patentability for corresponding PCT/CA2012/000203, issued Sep. 17, 2013.
Malic J. et al., Nanoimprinted plastic substrates for enhanced surface plasmon resonance imaging detection, 2009, Optics Express, vol. 17, No. 22, pp. 20386-20392.
Glinsner T. et al., Fully automated hot embossing processes utilizing high resolution working stamps, Microelectronic Engineering, 2009, vol. 87 No. 5-8 pp. 1037-1040.
English Abstract of EP2042467 published Apr. 1, 2009.
English Abstract of CN101571536 published Nov. 4, 2009.
English Abstract of CN101629143 published Jan. 20, 2010.
European Search Report issued in respect of corresponding European Application No. 12757703.9 mailed on Jul. 14, 2014.

* cited by examiner

MICROFLUIDIC SYSTEM HAVING MONOLITHIC NANOPLASMONIC STRUCTURES

CROSS-REFERENCE TO RELATED APPLICATIONS

This application is a national phase entry of International Patent Application PCT/CA2012/000203 filed Mar. 12, 2012 and claims the benefit of U.S. Provisional Patent Application Ser. No. 61/452,868 filed Mar. 15, 2011, the entire contents of both of which are herein incorporated by reference.

FIELD OF THE INVENTION

The present invention is related to microfluidic systems and devices having nanoplasmonic features, particularly for use in cell culture applications, and to processes of producing such systems and devices.

BACKGROUND OF THE INVENTION

Analysis of molecular binding and cell behavior are important for disease diagnostics, biomedical research, and drug discovery. The vast majority of array-based studies of bioaffinity interactions employ fluorescently labeled biomolecules or enzyme-linked colorimetric assays. However, there is a need for methods that detect bioaffinity interactions without molecular labels, especially for biomolecular and cellular interactions, where labeling is problematic and can interfere with their biological properties. The development of simple and specific biosensors to detect biomarkers and measure cellular response has far-reaching implications in their timely detection which is of great concern to human health and safety.

The advances in genomics and proteomics have unveiled an exhaustive catalogue of biomarkers that can potentially be used as diagnostic and prognostic indicators of genetic and infectious diseases. The antibody and nucleic acid fluorescence-based detection approaches currently consist of complex, multi-step, time consuming, and labor intensive assay formats and target analyte analysis to ensure the specificity of detection. Additionally, these methods are not suitable for the rapid pathogen or cancer detection as they require extensive blood culture of the pathogen or diseased tissue in the central laboratory prior to the detection of antibodies.

The analysis of bio-molecular interactions is also a key part of the drug discovery process which involves determining the binding affinity of the drug to the target protein of interest. Even though developments in the field of high-throughput screening (HTS) and computational chemistry greatly accelerated and facilitated the drug finding process, there are significant limitations to overcome. An example is the fluorescence-based HTS assay, which may generate false positive (e.g. binding to the reporter enzyme or direct hydrophobic interaction of the label with the target) or false negative results (e.g. occluding of the binding site). The application of novel and efficient label-free technologies is of high importance to the drug discovery process, since they will lower development costs and decrease the time to market.

For drug discovery as well as in the biomedical research, the study of the effect of the specific cues (e.g. chemical, topographical, flow, etc.) on cell attachment and motility, cell viability, cell proliferation and cell cycle is of paramount importance. Inducing and subsequent measurement of a specific cellular response requires providing the cells with the appropriate cues, to control the conditions in the cell microenvironment, and to monitor cellular responses on multiple hierarchical levels within a large number of parallel experiments. Currently employed assays that rely on cell culture in Petri dishes and subsequent fluorescence-based live-cell imaging and biomolecule detection are slow, cumbersome and cannot meet these requirements. Multi-well plate assays can increase the throughput through automatic imaging afforded by high content cell screening (HCCS). However, an important consideration for the multi-well assays is ensuring uniform patterning or treatment of each well which is often precluded by variations in the volume of liquid dispensed into each well. The resulting variability in the concentration of applied reagents hinders fair and quantitative comparisons and limits the ability of HCCS to resolve small differences in cell signaling responses. This issue is exacerbated in more complex protocols, such as sequential exposure of cells to different media, because of errors that accumulate when changing media. Moreover repeated media aspirations might unintentionally remove cells from the wells. Because these assays are also difficult to miniaturize, HCCS experiments may consume large quantities of expensive or valuable cells and reagents. Finally HCCS still relies on fluorescent tags which may trigger unwanted steric hindrance effects.

Consequently, the research into the effect of cues (single or multiple) on cellular response to date has been limited by the lack of robust and reproducible methods for homogeneous material production, precise control of the cell culture conditions and in situ real-time label-free monitoring of cellular response, cell behavior, cell viability or biomolecular binding interactions. Specifically, the material production methods have lacked the control required to reproducibly fabricate homogeneous surfaces that will allow investigations into specific interactions between cells and isolated variables i.e. a precisely defined nanoscale patterns in a defined space with control over the induced change in topography and associated changes to surface energy. The commonly employed well-based cell culture methods are costly and suffer errors in liquid dispensing, both manually and robotically, thus precluding uniform handling of each well which in turn limits how finely signaling responses may be resolved. Finally, while the use of fluorescent imaging techniques for cell analysis can provide information not easily attainable by other methods, they are usually confounded by the need to over-express the signaling protein of interest and by possible effects of the fluorescent marker on the protein's function. Therefore due to the phenomenological nature of current studies, the responses achieved have been heterogeneous at both single cell and cell population levels (Balasundaram 2007; Barbucci 2003; Blümmel 2007; Curtis 2006; Dalby 2007a; Ernsting 2007; Kimura 2007; Salber 2007).

Fluorescence and chemiluminescent detection are the most common methods employed for biomolecule recognition. Both schemes require the use of a labeled recognition element which binds to a molecule of interest thus producing a selective signal upon binding (Marquette 2006). Currently, the detection and quantification of genomic and proteomic biomarkers from serum or other physiological samples rely on solid-phase detection, where strong amplification chemistry is often needed to produce a readout. In the case of DNA markers, the state of the art relies on polymerase chain reaction (PCR), while for the protein markers enzyme-linked immunosorbent assay (ELISA) prevails. Many attempts at miniaturizing bench-top systems using microfluidics in order to increase the detection limits and reduce incubation times, reagent consumption and sample size have been reported with impressive results (Zhang 2009a; Zhang 2009b; Lim 2007; Lee 2006; Malic 2007). However, despite a growing focus from the microfluidic research community, both PCR and ELISA rely on fluorescence labels, which increase the complexity and cost of the assay. In addition to the requirement for a labeled recognition element, these techniques typically require complex optical systems which typically consist of a large microscope or a microplate reader. As a result, the field of microfluidics has yet to produce many commercial devices for disease diagnostics (Myers 2008). There is a need for coupling and integrating microfluidics with direct label-free detection methods that base themselves on physical characteristics of biologic phenomena and have the potential to reduce reagent costs and test complexity (Weigl 2008).

The development of minimally invasive techniques to induce a specific cellular response is focused on controlling the direct contact and interaction between a given cell type and a well defined material. One way of controlling cell adhesion and subsequent morphology is by nanotopography. Research has shown that cells can detect and respond to an array of topographies and can be affected by the level of order of an induced topography, with clear effects on cell functionality (Dalby 2009; Dalby 2008; Dalby 2007b; Dalby 2007c; Dalby 2007d; Hochbaum 2010). Similarly, bacteria also respond to topographical (spatial and mechanical) cues and spontaneous bacteria patterning on a periodic nanostructure array has recently been shown (Hochbaum 2010). Another method employs chemically modified surface to induce cellular response (Cavalcanti-Adam 2008). For both strategies to prove successful the material must be homogenous, robust and fabricated or functionalized in a reproducible manner. To date, several methods have been used for this purpose, including electron-beam lithography, nanoimprint lithography and dip-pen nanolithography (Cavalcanti-Adam 2007; Curran 2010). However, the assays in these studies were performed using traditional cell-culture methods and analyzed using live fluorescence microscopy with inherent drawbacks of these techniques which may have resulted in misleading interpretation of results due to error in liquid handling, perturbation caused by fluorescent markers and low throughput in which only a few cells were imaged for each experimental run.

Flow cytometry (FC) and laser scanning cytometry (LSC) are the most widely used techniques for cell analysis with well characterized distributions of cellular behaviour. Both techniques use fluorescent dyes to label biomolecules of interest within the cell in order to reveal the information about the quantity of biomolecules within the cell. Flow cytometry involves the hydrodynamic isolation of individual cells thus affording high throughput serial analysis. However, FC is limited to characterizing fluorescent signals (GFP-fusion proteins, immunofluorescence, and fluorogenic substrates to intracellular enzymes) (Fayet 1991; Nolan 1998; Krutzik 2006), which can lead to steric hindrance and is incapable of important time-dependent measurements of the cell population. Conversely, laser scanning cytometry (LSC) relies on the use of a scanning laser to excite the dyes on surface immobilized cells (Griffin 2003; Bedner 1993) thereby allowing kinetic measurement of time-dependent information in individual cells. However, only a limited region of a plate can be scanned thus limiting the throughput of the technique. Additionally, the introduction of reagents is performed using a pipette and only slow time dependent changes after solution exchange are meaningful. This is particularly due to uneven introduction of solution over the whole slide or plate, and the serial process of laser scanning. Furthermore, cells analyzed using both methods are usually grown in traditional flasks, slides or Petri-dishes before analysis, and so uniformity of environment is limited to that of the flask or dish. Notably, cell-cell contact is not controllable, and diffusible secretions are maintained in the culture environment.

To overcome some of these limitations, research has recently shifted towards the exploitation of the precise chemical delivery capabilities of microfluidic devices. The single most popular approach for the fabrication of microfluidic devices for cell-based assays is based on the soft-lithography of polydimethylsiloxane (PDMS). PDMS is an elastomer which is casted over a mold typically fabricated using photolithography and cured for several hours resulting in a transfer of features from the mold to the PDMS. Its wide use as a material of choice is due to its mechanical property, which is amenable to integration of fluidic valves, essential elements for major microfluidic applications. PDMS platforms for cell culture have been reported in the past especially for two-dimensional morphological cells, such as epithelial cells, and several designs have been the subject of patent applications (Jin 2010; Lee 2010). However, most of these studies coupled microfluidic device to traditional macroscale equipment (i.e. fluorescence microscopes) and relied on the use of fluorescence imaging for cellular response analysis.

Moreover, there is surprisingly little work reported on the combination of nanopatterned surfaces and microfluidics, especially in a way advantageous for studying topographically induced cellular response. This is in part due to the difficulty in reproducibly fabricating nanostructured surfaces within microfluidic cell culture devices. Several production processes have been reported for nanostructure fabrication inside microchannels including vapor deposition of nanoparticles (Song 2009), in situ formation of nanoparticles inside the channels from catalytic reaction (Fonverne 2009), and polymerization of a polymer around an anodic aluminum oxide template (Soper 2008). However, controlling the regularity, geometry and/or spacing of the nanoparticle arrays using these techniques is difficult to achieve limiting the reproducibility of the experimental measurements.

In order to obtain spatially controlled geometry and spacing of the nanostructures within a PDMS microfluidic channel, multilayer mold comprising nano- and micro-structures are required with fabrication procedures involving sequential electron-beam lithography, interference lithography or nanoimprint lithography in concert with photolithography of SU-8 resist. The compatibility of materials and reagents involved in these processes is difficult to achieve. Additionally, once the mold is fabricated and the microchannels have been defined, the slightest change of the microfluidic layout would require the repetition of complete fabrication process, starting with the nanostructured substrate. This can result in topographical surface variations induced by sample-to-sample fabrication differences. Furthermore, PDMS soft-lithography fabrication technique itself is not well suited for mass production of microfluidic devices which hinders their application in industry, including medical diagnosis and pharmaceutics. Finally, the use of PDMS as a material for in vitro models for cell culture needs to be considered in a biological context due to the leaching of uncured oligomers from the polymer network into microsystem media (Regehr 2009).

Further, microfluidic devices with nanostructured hydrophobic surfaces have been developed to control surface tension and liquid pressure in fluid flow channels (Extrand 2005), but the standard techniques used to nano-pattern the channel surfaces are insufficiently flexible to permit simple and fast patterning of nanostructures, especially different nanostructured patterns, at specific locations in the channels or chambers of the device but not at others. Thus, different design features within the same device are difficult to accomplish and the designs are difficult to adapt to the requirements of plasmonic detection techniques.

In general, prior art systems have one or more deficiencies. There is a lack of an integrated microfluidic system that relies on non-invasive, label-free detection technologies including plasmonic techniques such as surface plasmon resonance (SPR) (e.g. reflection-mode SPR, transmission-mode SPR, localized surface plasmon resonance (LSPR)) and surface-enhanced Raman spectroscopy (SERS) for monitoring cell behavior, cell-substrate interactions, cell response to stimuli and biomolecule detection. There is a lack of fabrication techniques allowing monolithically integrated nanostructured cell culture system in long-term biocompatible materials with simultaneous cell guiding functionality and plasmonic detection capability using topographical cues and nanostructure plasmonic response, respectively. There is poor control of cellular microenvironment in Petri-dish or microwell plates. There is lack of reproducible and robust surface topography (nanopatterning) for precise control of cellular response and cell-substrate interaction studies. There is a lack of integrated nanostructured surface within microfluidic channels. And, there is a lack of low-cost and rapid mold fabrication techniques that allow interchangeable nano- and micro-structure design.

There remains a need for an integrated system that can meet one or more of the following requirements: (i) efficient control of initial cell adhesion; (ii) efficient control of the cellular response to the specific stimulus over a prolonged period; (iii) in situ, label-free and real-time monitoring of cellular response, cell mobility, cell behavior, cell-viability or biomolecule detection in order to avoid false response due to cellular secretion of the molecules to which they respond and steric hindrance induced by the fluorescent tags. Additionally, the system is ideally low-cost, portable and amenable to mass-production.

SUMMARY OF THE INVENTION

In one aspect of the present invention, there is provided a process of producing a patterned polymeric substrate comprising: etching one or more ordered patterns onto a hard substrate, the ordered patterns comprising ordered arrays of nano-scale elements having cross-sectional dimensions in a range of from 10 nm to 1000 nm, the arrays having a spacing distance between their respective elements where cross-sectional dimension to spacing distance ratio is greater than 0.2; micro-patterning a polymeric film to form a membrane comprising a first surface bearing a pattern of micro-scale and/or meso-scale features for defining one or more channels and/or chambers, one or more of the micro-scale and/or meso-scale features comprising through-holes; placing the membrane on the hard substrate with a surface opposite the first surface against the hard substrate, the through-holes aligned to expose the one or more ordered patterns, and applying pressure sufficient to seal lips of the membrane surrounding the through-holes against the hard substrate; placing a settable liquid polymer or metal in the through-holes and over the first surface and setting the settable liquid polymer or metal to form a stamp from the settable liquid polymer or metal, the stamp comprising micro-scale and/or meso-scale reliefs for defining one or more channels and/or microfluidic chambers and further comprising one or more nano-scale relief patterns on the micro-scale and/or meso-scale reliefs that complement the one or more ordered patterns; and, patterning a polymeric substrate by stamping the polymeric substrate with the stamp to form the one or more channels and/or microfluidic chambers in the polymeric substrate, the polymeric substrate comprising one or more surfaces having one or more ordered patterns that are substantially identical to the one or more ordered patterns etched onto the hard substrate, the one or more ordered patterns in the polymeric substrate suitable for plasmonic resonance reading of a fluid within the one or more channels and/or chambers.

In another aspect of the present invention, there is provided a stamp for patterning a polymeric substrate, the stamp comprising: a polymer or metal of sufficient hardness to be able to pattern the polymeric substrate; and, a pattern of micro-scale and/or meso-scale reliefs for forming one or more channels and/or microfluidic chambers, one or more of the micro-scale and/or meso-scale reliefs having top surfaces comprising one or more nano-scale relief patterns for forming one or more ordered arrays of nano-scale elements in the polymeric substrate, the nano-scale elements having cross-sectional dimensions in a range of from 10 nm to 1000 nm, the arrays having a spacing distance between the elements where cross-sectional dimension to spacing distance ratio is greater than 0.2.

In yet another aspect of the present invention, there is provided a microfluidic device comprising a monolithic polymeric substrate patterned with one or more micro-scale channels in fluid communication with one or more microfluidic chambers, a surface in the polymeric substrate comprising an ordered array of nano-scale elements suitable for plasmonic resonance reading of a fluid on the surface, the nano-scale elements having cross-sectional dimensions in a range of from 10 nm to 1000 nm, the array having a spacing distance between the elements where cross-sectional dimension to spacing distance ratio is greater than 0.2.

Microfluidic devices of the present invention are monolithic microfluidic structures in a polymeric substrate having nanostructures monolithically integrated in the substrate. The devices have at least one micro-scale channel in fluid communication with at least one microfluidic chamber. Channels include, for example, sample loading channels, cell loading channels, medium perfusion channels, mixing channels, particle separation or fractionation channels, gradient generating channels and high resistance perfusion conduits, which may have different channel dimensions dictated by the specific application. Microfluidic chambers include, for example, cell culture chambers, bacteria or cell capture chambers, biomolecular interaction chambers or mixing chambers. Other microfluidic structures may also be present, for example valves and pumps for controlling fluid flow, conduits, inlets, outlets, and the like.

At least one surface in a channel or microfluidic chamber of the device is patterned with an ordered array of nano-scale elements suitable for plasmonic resonance reading of a fluid on the surface. More than one surface may be patterned and the pattern may be the same or different. The patterned surface or surfaces may be anywhere in the device, and could even be everywhere in the device. The location of the patterned surface or surfaces is dictated by the ultimate use of the device. Such patterned surfaces may be called "nanoplasmonic surfaces", and the elements may be called "nanoplasmonic elements". The nano-scale elements may serve a dual purpose as both nanoplasmonic elements and nano-topographical cues. To function as a nanoplasmonic surface, the ordered array of nano-scale elements has a highly regular or periodic pattern designed to have a specific plasmonic resonance to permit label-free, real-time optical reading using plasmonic techniques. The regularity of the pattern is reflected in very consistent size, spacing and/or geometry of the nano-scale elements, and arises from the highly reproducible process employed in the present invention to produce the patterned polymeric substrate of the device. Preferably, for each of the size, spacing and/or geometry of the elements in the array, the standard deviation from the respective average is no more than about 3%, preferably no more than about 2.5%, and may be no more than about 1%.

The nano-scale elements have cross-sectional dimensions in a range of from about 10 nm to about 1000 nm, which is in the nano-scale range. Preferably the cross-sectional dimensions are in a range of from about 10 nm to about 750 nm. Individual nano-scale elements preferably have an aspect ratio (height to width) of about 100 or less, more preferably 50 or less, yet more preferably 10 or less. Aspect ratios may be in a range of from 100:1 to 1:100, 50:1 to 1:50 or 10:1 to 1:10.

Spacing of nano-scale elements in the ordered array is an important factor in maintaining suitable regularity for plasmonic resonance reading techniques. Ideal spacing distance is dependent on the size of the nano-scale elements. For plasmonic techniques, cross-sectional dimension to spacing distance ratio is generally greater than about 0.2. Preferably, the ratio of cross-sectional dimension to spacing distance is in a range of from about 0.2 to about 1.5, or about 0.5 to about 1. The ratio of cross-sectional dimension to spacing distance is commonly about 0.5 or about 1.

The nano-scale elements may have any nanostructure geometry suitable for the reading technique to be used. Suitable geometries include, for example, nanopillars, nanoposts, nanodots, nanorods, nanopyramids, nanocrescents, nanodisks, nanodomes, nanoholes, nanogratings or nanogrooves. Multiple arrays having different nanostructure geometries for different functionalities (e.g. gratings for light-coupling or nanopillars for SPR electromagnetic field enhancement) can be integrated within the same device. Multiple arrays having different nanostructure geometries can be co-mingled to occupy the same surface, or different arrays can be on different surfaces in the device. Different arrays can resonate at different wavelengths permitting implementation of a multiple frequency interrogation scheme for parallel multichannel detection of different targets.

Ordered arrays of nano-scale elements may be integrated onto a surface of micro-scale features (e.g. micropillars) in the device. In cell culture applications, this can provide two levels of topographical cues (spatial and mechanical cues) on the micro- and nano-scales for control of cell attachment and motion while retaining plasmonic detection capability for studying cell behavior and interactions. Further, micro-optic features (e.g. microlenses, blazed gratings, etc.) may be formed into the microfluidic device for various purposes, including enhancing light coupling or improving light collection efficiency, depending on the particular reading techniques used.

Nano-scale elements may be further treated to enhance or alter the properties of the ordered array. Such treatments may include, for example, metallization of the nano-scale elements to increase reflectivity of the array or chemical surface modification to permit attachment of biomolecules. For plasmonic techniques, metallization of one side of the nano-scale elements to form single-sided metallic nano-elements is particularly preferred. Silver, gold, copper, platinum and palladium are preferred metals for metallization, particularly for SERS applications. Metallization may be accomplished by any suitable method, for example, evaporation, sputtering or electroplating. Chemical surface modification includes modification with specific reactive end-groups, for example —COOH, —OH, —$NH_3$, -biotin, -silane, etc., to enable subsequent attachment of antibodies, oligonucleotides, aptamers or proteins for cell, bacteria or biomolecule capture.

The polymeric substrate may comprise any polymeric material that is soft enough to be stamped by the stamp. Preferably, the polymeric material is suitable for fabrication of microfluidic devices. Preferably, the polymeric material comprises a cyclo-olefin polymer (e.g. Zeonor™), a thermoplastic polymer (e.g. polyolefins), a biodegradable polymer (e.g. starch, poly-lactic acid), an elastomer (e.g. thermoplastic elastomer (TPE) or any blend thereof. More preferably, the polymeric material comprises a cyclo-olefin polymer (COP) (e.g. Zeonor™) or a thermoplastic elastomer (TPE).

The stamp may comprise any polymer or metal that is settable from liquid form to produce a polymer or metal that is harder than the polymeric substrate and hard enough to impress the ordered pattern on the polymeric substrate. If a metal is used, the metal in its liquid state must not be hot enough to melt the hard substrate and polymeric film. Preferably, a settable polymer is used and the polymer is a curable polymer, preferably a curable thermoset polymer. The polymer for the stamp may be settable or curable thermally, chemically or with light. Photo-curable polymers, especially ones cured by UV light, are particularly preferred. Some examples of photocurable polymers include MD-700 and Darcour™ blend. The stamp is used to transfer all of the features of the microfluidic device into the polymeric substrate in one processing step. The processing step may involve any suitable method for patterning polymeric substrates using stamp or dies, for example, hot embossing, nanoimprint lithography or injection moulding. The stamp may be treated to facilitate patterning of the substrate, for example, treating the stamps with a release agent can facilitate separation of the patterned polymeric substrate from the stamp. Since the stamp comprises reliefs for all of the features of the microfluidic device, the microfluidic device can be formed completely in one step resulting in a monolithic device having all of the features of the device integrated into the polymeric substrate. Further, the stamp can be re-used to make more devices and the use of the stamp provides pattern and dimensional consistency between devices produced in different production runs. These are distinct advantages over prior art processes for producing microfluidic devices.

The stamp may be fabricated from a master mold by transferring features from the master mold to the settable polymer. The master mold comprises a hard substrate and one or more membranes placed on the hard substrate. The hard substrate may comprise a metal, a silicon wafer, a glass substrate or a hard polymer. The term "hard substrate" refers to a substrate that is harder than the membranes placed on the substrate. Preferably, the hard substrate comprises a hard polymer, for example, a cyclo-olefin polymer (e.g. Zeonor™), a polymethylmethacrylate (PMMA), a polycarbonate (PC) or a polyetheretherketone (PEEK). The one or more membranes comprise polymeric films of a soft polymer, for example, polydimethylsiloxane (PDMS), a soft thermoplastic polymer (e.g. a soft polyolefin) or a soft thermoplastic elastomer (e.g. Kraton™, Mediprene™, CL-30 or styrene-ethylene-butadiene-styrene (SEBS)). The polymeric films are preferably films of soft thermoplastic elastomer (TPE). The term "soft polymer" refers to a polymer that is softer than the hard substrate.

One or more ordered patterns comprising nano-scale elements are etched onto the hard substrate. Etching can be accomplished by any suitable means appropriate for the hard substrate. For example, etching may be accomplished with lasers, with ion bombardment or with chemical etching, for example reactive ion etching, deep reactive ion etching, wet chemical etching, electron beam lithography, nanoimprint lithography, ion beam milling, laser ablation or interference lithography. The membranes comprise polymeric films having one surface onto which micro-scale and/or meso-scale features have been micro-patterned. Patterning of the polymeric films may be accomplished by any suitable means, for example, hot embossing, injection moulding, nanoimprint lithography or roll-replication. The micro-scale and/or meso-scale features in the membranes define one or more microchannels and/or microfluidic chambers that will eventually be created in the final microfluidic device. One or more of the features patterned in the polymeric film may be through-holes that are aligned to expose the one or more ordered patterns on the hard substrate. The through-holes have the shape of the microfluidic features (e.g. microchannels, microfluidic chambers, micropillars, etc.) that are intended bear the ordered patterns in the final device.

The membranes are placed on the hard substrate so that the surfaces bearing the micro-scale features are also exposed. More than one membrane may be stacked on the hard substrate and the through-holes aligned with the ordered patterns to obtain the desired microstructural features in the device. Use of stacked membranes is particularly useful for forming microstructural features, such as micropillars, having a top surface covered with the nano-scale elements. When placing the membranes on the hard substrate, a seal around the through-holes may be achieved by applying sufficient pressure to seal lips of the membrane surrounding the through-holes against the hard substrate.

The master mold thus formed may be used to fabricate the stamp by placing the settable polymer in the through-holes and on the membrane surface onto which the micro-scale and/or meso-scale features have been micro-patterned. The settable polymer is typically poured or injected in liquid form onto and into the master mold and then set as described above. In this manner, the settable polymer is in contact with the features on the membrane and the ordered pattern on the hard substrate, so when the settable polymer hardens, the micro-scale and/or meso-scale features and the ordered pattern of nano-scale elements are transferred to the set polymer. Once the settable polymer has hardened, the stamp so fabricated can be demolded and then used to pattern the polymeric substrate to form the final device. Thus, the master mold is an exact replica of the final device, and the stamp is the toll used to transfer the pattern in the master mold to the polymeric substrate to produce the final device. It is an advantage of the present invention that when a different channel layout needs to be used with the same ordered pattern of nano-scale elements, the new master mold can be easily fabricated by delaminating the soft membranes from the hard substrate an replacing the membranes with membranes having the new layout.

The present invention advantageously provides low-cost monolithic integrated microfluidic systems with multiplexing capability (e.g. valving, pumping) for precise control of cell culture conditions that can simultaneously integrate label-free enhanced plasmonic techniques such as surface plasmon resonance (SPR) (e.g. reflection-mode SPR, transmission-mode SPR, localized surface plasmon resonance (LSPR)) or surface-enhanced Raman scattering (SERS). The present monolithic integrated polymer-based microfluidic system has micro- and nano-structures that provide topographical cues for cell attachment and culture for controlling cell behavior while permitting monitoring of cellular behavior, motility, attachment, viability, biomolecule interactions or any combination thereof using plasmonic detection. The system is fabricated using a simple, robust and cost-effective process in a single step.

The present system is advantageous over both conventional and recently reported processes employed for cell culture and monitoring of cell behavior as the present system integrates in a single monolithic biocompatible substrate both a nanostructured surface required for plasmonic response monitoring and a network of microchannels for precisely controlling cellular environment, with additional advantages of low-volume consumption, rapid low-cost fabrication of molds with easily interchangeable microfluidic channel layouts, amenability to mass production, and in situ label-free real-time detection of cellular response, viability, behavior and biomolecular binding using enhanced SPR (reflection-mode SPR, transmission-mode SPR, LSPR) or SERS.

The present invention has application to such problems as screening molecular or cellular targets, cellular identification, screening single cells for RNA or protein expression, monitoring cell response to different stimuli (chemical, topographical, flow, etc.), genetic diagnostic screening at the single cell level, or performing single cell signal transduction studies.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 3 depicts SEM micrographs of fabricated structures showing (a) different possible nanoplasmonic nanostructures including nanoholes, nanopillars, nanoposts and nanogratings, (b and c) three-dimensional micro- and nano-structures defined in a single substrate using a one step fabrication process of the present invention.

DESCRIPTION OF PREFERRED EMBODIMENTS

Example 1

Figure 1:
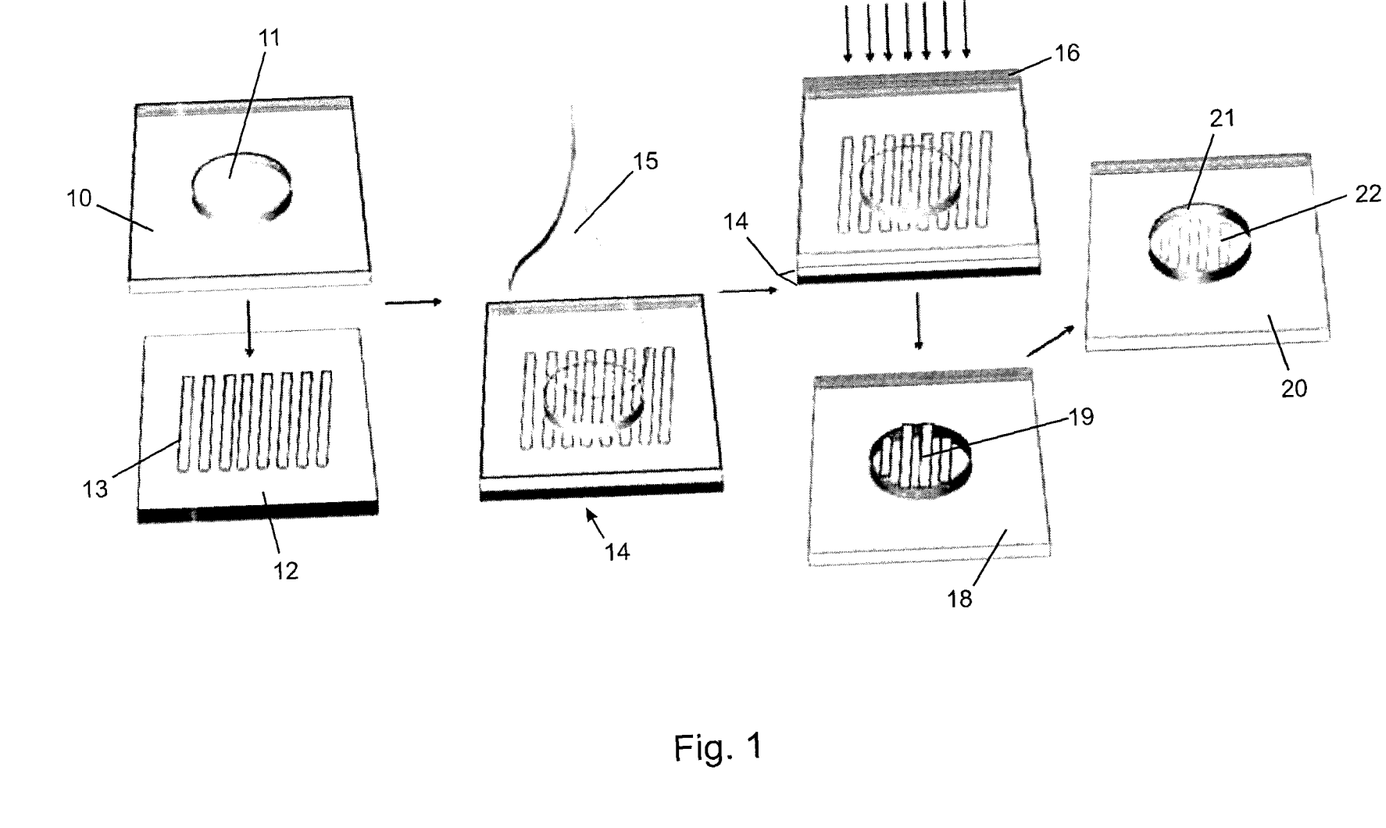
FIG. 1 depicts a schematic diagram of a process of the present invention for producing a monolithic integrated nanoplasmonic microfluidic cell culture system.

Process for Fabricating a Monolithic Integrated Nanoplasmonic Microfluidic Cell Culture System A monolithic integrated nanoplasmonic microfluidic cell culture system of the present invention may be produced generally as shown in FIG. 1, which illustrates the process showing a single cell chamber and none of the channels, conduits, valves or other microfluidic features for clarity. A soft thermoplastic elastomer film is hot-embossed to form micro-scale and meso-scale features (microchannels, conduits, chambers, etc.) in TPE membrane 10 including through-hole 11. This is performed at an applied pressure ranging from 5 kN to 15 kN, for 5-30 min, at a temperature in a range of from 100° C. to 160° C., depending on the desired features. Hard Zeonor™ substrate 12 is patterned by hot-embossing at an applied pressure of 10 kN to 20 kN for 10-30 min at a temperature ranging from 140° C. to 170° C. depending on the specific Zeonor™ grade to form a regular array of nano-scale grating elements 13. With the micro-scale and meso-scale features facing up, the TPE membrane is placed on the Zeonor™ substrate such that the through-hole is aligned with the grating elements. The membrane is then reversibly bonded to the Zeonor™ substrate to seal the membrane around the through-hole against the Zeonor™ substrate to form master mold 14 at room temperature. Photocurable polymer 15 is poured into the through-hole and onto the membrane to cover the membrane and the micro-scale and meso-scale features thereon. Glass or metal backing plate 16 is placed over top of the photocurable polymer and the photocurable polymer is then exposed to UV radiation 17 to cure the polymer. When a metal backing plate is used, the assembly is flipped upside down to UV cure the polymer. After curing, master mold 14 and glass (or metal) plate 16 are removed to provide working stamp 18 having reliefs 19 comprising a reverse image of the micro-scale and meso-scale features and the regular array of nano-scale grating elements. The working stamp is then used to hot-emboss "hard or soft" thermoplastic polymer substrate 20 (e.g. Zeonor™, PMMA or a thermoplastic elastomer such as CL-30, Mediprene™, etc.) to provide, in one step, a monolithic microfluidic cell culture system having micro-scale and meso-scale features 21 and regular array of nano-scale grating elements 22 therein.

Figure 2:
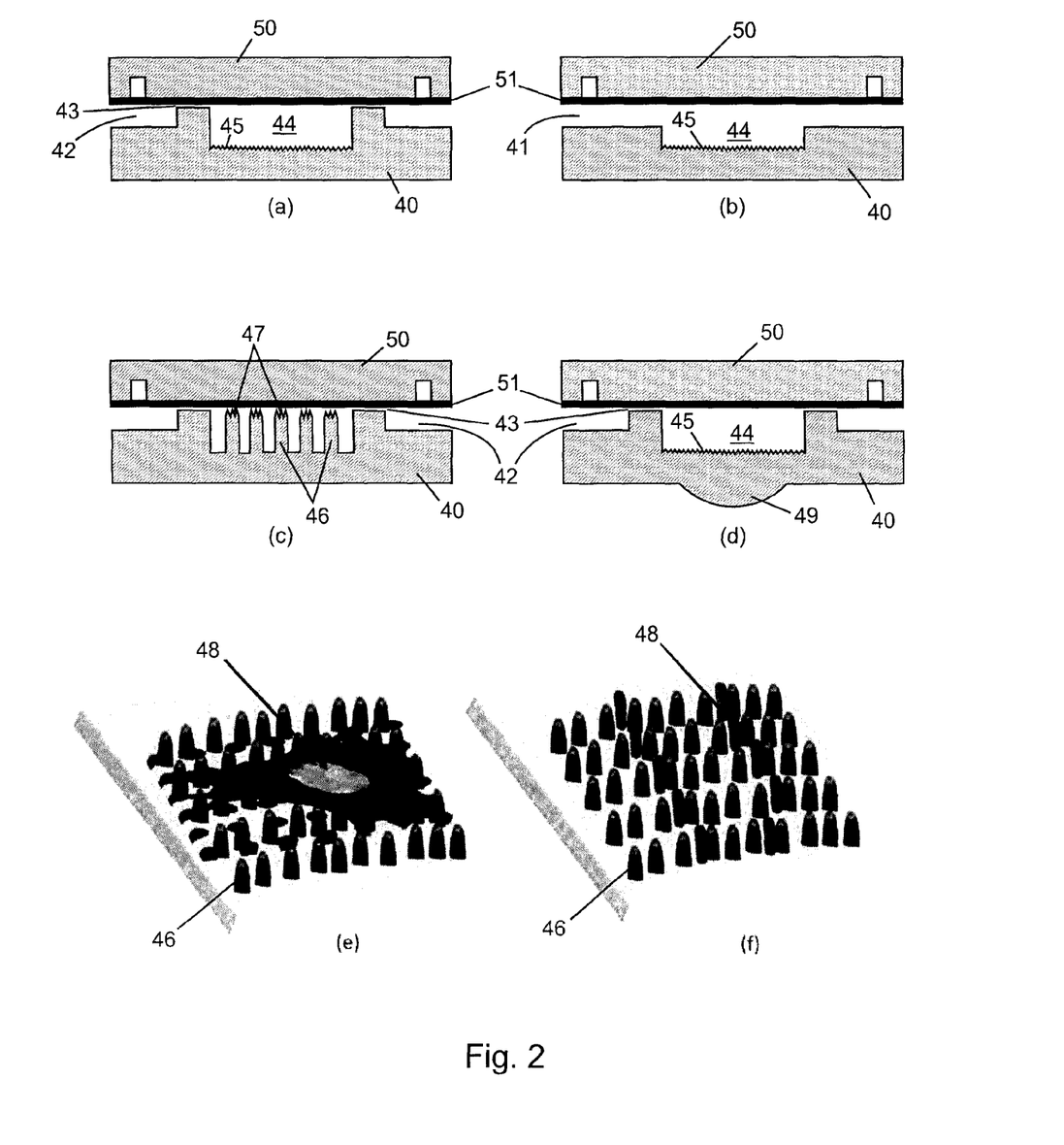
FIG. 2a-d depict cross-section schematics of a nanostructured nanoplasmonic microfluidic cell culture system, where (a) is a cross-section of a chamber through a perfusion channel and perfusion conduit, (b) is a cross-section of a chamber through a cell-loading channel, (c) is a cross-section through a chamber showing integrated micropillars with nanostructured top surface and (d) is a cross-section through a chamber showing an integrated micro-optic element on the bottom side of the flow layer substrate.
FIG. 2e-f depict 3D views of the chamber bottom depicted in FIG. 2a containing micropillars with nanostructured top surface area used to (e) control cell attachment/motility and (f) study cell-substrate interactions.

Microfluidic cell culture systems produced in this manner may comprise any number of cell culture chambers, microchannels, conduits, valves, etc. More detailed schematic drawings of one cell culture chamber in the monolithic integrated nanoplasmonic microfluidic cell culture system produced by this process are shown in FIG. 2. Referring to FIGS. 2a to 2d, flow layer 40 of the cell culture system comprises cell loading channels 41, perfusion channels 42, perfusion conduits 43 and culture chambers 44, which have different dimensions dictated by the specific application. As shown in FIGS. 2a, 2b and 2d, the bottom of the cell culture chambers may be patterned with an ordered array of nanostructures 45, in this case a nanograting. Alternatively, as shown in FIG. 2c, the bottom of the cell culture chamber may have integrated micropillars 46 having nanostructures 47 patterned thereon. As shown in FIGS. 2e to 2f, such nanostructured micropillars can provide two-levels of topographical (spatial and mechanical) cues on the micro- and nano-scale for controlling attachment/motion (cell isolation or confinement) of cells 48, while retaining plasmonic detection capability for the study of cell behavior and interactions. Further, as shown in FIG. 2d, flow layer 40 can be fabricated to include micro-optic elements, such as microlens 49 of nanograting 45, for enhanced light coupling or improved light collection efficiency, depending on the particular interrogation scheme (e.g. transmission or reflection SPR, LSPR or SERS).

Control layer 50 and thin membrane 51 may be placed on top of flow layer 40 to control fluid flow in the channels and conduits of the microfluidic cell culture system. Control layer 50 contains a network of channels used to supply pressure on thin membrane 51 sandwiched between the control layer and the flow layer in order to close the valves and control fluid flow. While for certain application, the use of valves for fluidic management might not be necessary, for high-level microfluidic integration of the system it is of great importance in order to allow two-dimensional addressing of each individual chamber. The monolithic integration of nanostructures with the flow layer allows the use of the control layer for the integration of valves which would otherwise be impossible by simply assembling a bottom nanostructured SPR layer with a top microfluidic structure.

Figure 3:
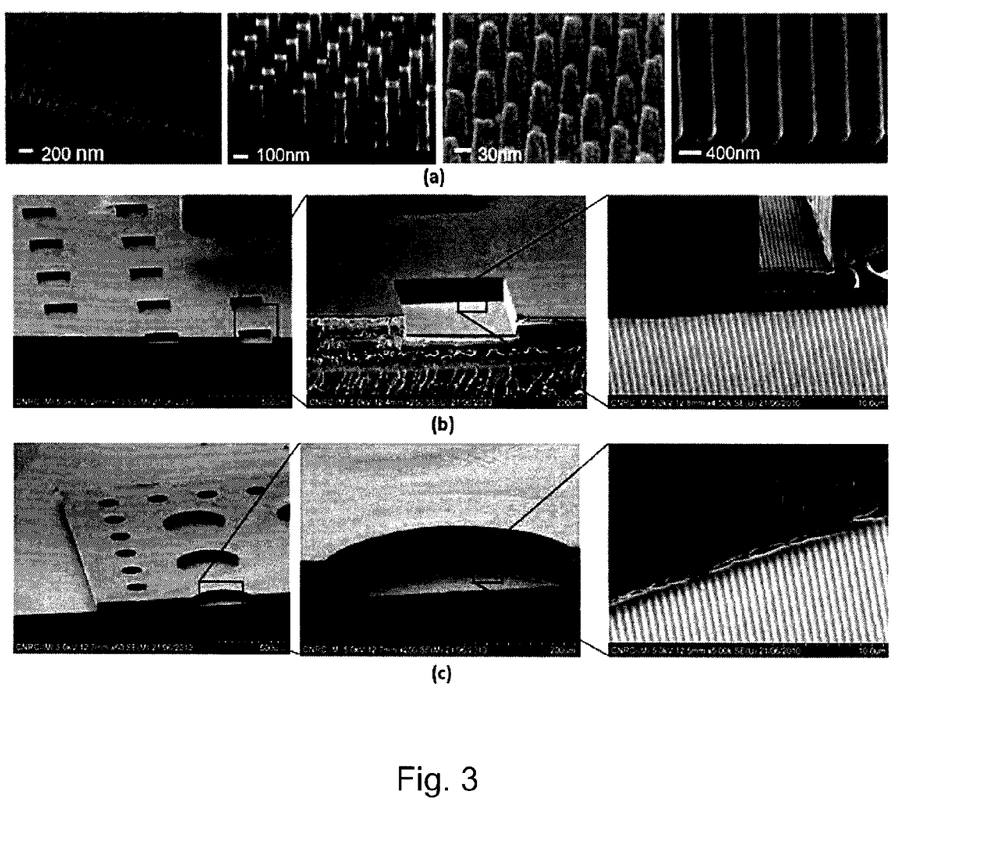

Referring to FIG. 3, sample scanning electron microscope (SEM) micrographs of possible nanostructures and their monolithic integration within microfluidic chambers of the microfluidic cell culture system are shown. In FIG. 3a, from left to right are shown nanoholes, nanopillars, nanoposts and nanogratings. In each of FIGS. 3b and 3c from left to right are shown successive magnifications of SEM micrographs of monolithic three-dimensional microstructures and nanostructures fabricated using the present method, where the SEM on the left shows the microstructures, the SEM on the right shows the nanostructures in a microstructure and the SEM in the middle has a magnification in between the left and right. In 3b and 3c, the SEM in the middle has a magnification 2.5× greater than the SEM on the left, and the SEM on the right has a magnification 20× greater than the SEM in the middle. The field of view for the SEM on the left is 500 μm.

Example 2

Use of a Monolithic Integrated Nanoplasmonic Microfluidic Cell Culture System in Plasmonic Detection In operation a monolithic integrated nanoplasmonic microfluidic cell culture system of the present invention employs pressure-driven flow to transport cells in suspension from a plurality of reservoirs through a plurality of cell-loading channels to a plurality of nanostructured cell culture chambers by closing valves of the perfusion channels and opening valves on the cell-loading channels. A plurality of cell-lines are loaded using a plurality of different reservoirs. Following initial cell attachment on the bottom of the nanostructured chambers, the valves on the cell-loading channels are closed, and fresh media is continuously injected in each of the perfusion channels. Multiple high resistance perfusion conduits ensure equal distribution of the media within the chamber while minimizing the shear-stress exerted on the cells.

Figure 4:
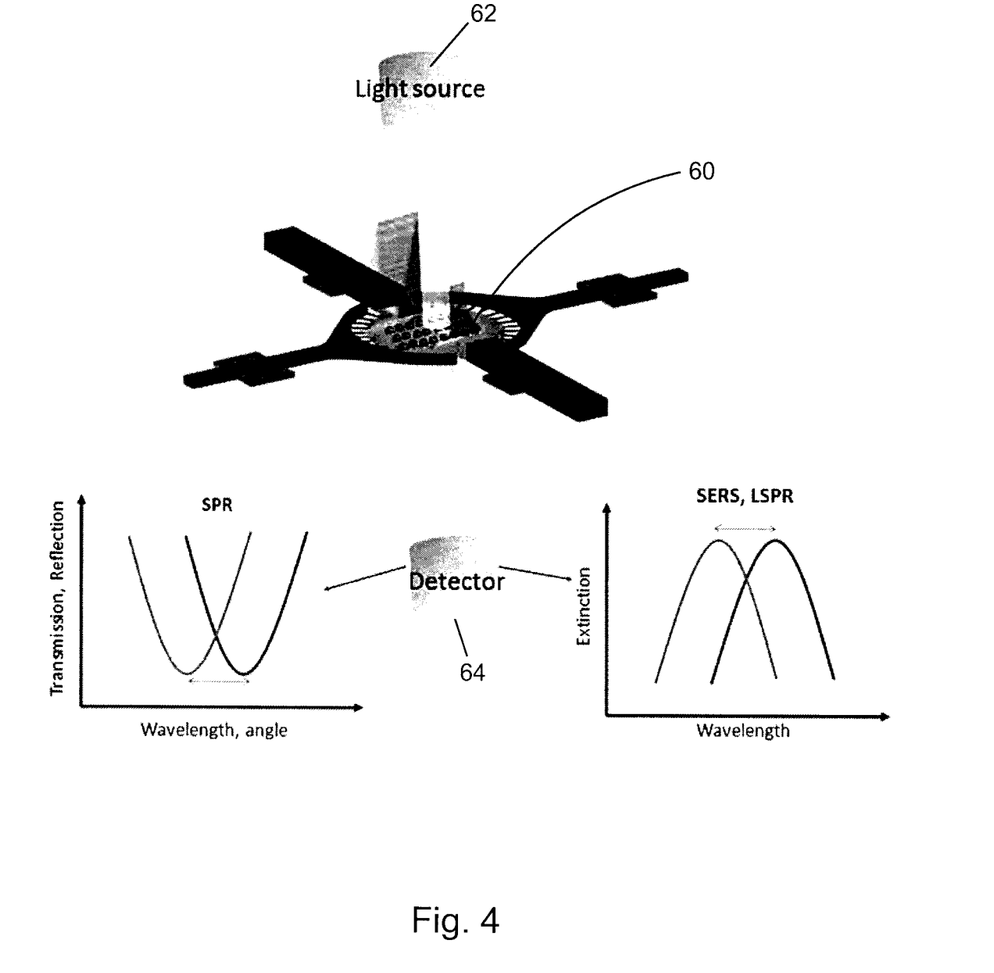
FIG. 4 depicts a schematic of a nanoplasmonic microfluidic cell culture system with plasmonic detection capability.

Once the cell culture chambers are loaded with cells, plasmonic resonance readings are taken using optical detection methods of Reflection or Transmission-mode Surface Plasmon Resonance, Localized Surface Plasmon Resonance or Surface Enhanced Raman Spectroscopy. FIG. 4 illustrates the configuration of microfluidic device 60 in relation to light source 62 and detector 64 of the optical detection method. With these detection methods, cell-substrate interaction can be monitored in situ, in real-time and without any labels by analyzing the shift in the plasmonic peaks of the nanostructured substrate response. Resulting shifts in plasmonic peaks for surface plasmon resonance (SPR) and localized surface plasmon resonance (LSPR) or surface enhanced Raman spectroscopy (SERS) are illustrated at the left and right, respectively, in FIG. 4.

Additionally, the present design allows monitoring of cellular response due to different bio-chemical cues which can be supplemented in the perfusion media. Furthermore, prior to cell loading, using the same microchannels, the bottom of the chambers can be functionalized by flowing different chemicals and/or biological species for monitoring of cell-substrate interactions or for the detection of biochemical targets excreted or extracted from the cell.

REFERENCES

The contents of the entirety of each of which are incorporated by this reference.

Balasundaram G, Webster T J. (2007) *J. Biomed. Mater. Res.*, Part A. 80a, 602-611.
Barbucci R, Pasqui D, Wirsen A, Affrossman S, Curtis A, Tetta C. (2003) *J. Mater. Sci.* 14, 721-725.
Bedner et al. (1998) *Cytometry.* 33, 1-9.
Blümmel J, Perschmann N, Aydin D, Drinjakovic J, Surrey T, Lopez-Garcia M, Kessler H, Spatz J P. (2007) *Biomaterials.* 28, 4739-4747.
Cavalcanti-Adam E A, Volberg T, Micoulet A, Kessler H, Geiger B, Spatz J P. (2007) *Biophys. J.* 92, 2964-2974.
Cavalcanti-Adam E A, Aydin D, Hirschfeld-Warneken V C, Spatz J P. (2008) *HFSP J.* 2, 276-285.
Curran J M, Stokes R, Irvine E, Graham D, Amro N A, Sanedrin R G, Jamil H, Hunt J A. (2010) *Lab on a Chip.* 10, 1662-1670.
Curtis A S, Dalby M J, Gadegaard N. (2006) *J. R. Soc. Interface.* 3, 393-398.
Dalby M J, Gadegaard N, Tare R, Andar A, Riehle M O, Herzyk P, Wilkinson C D, Oreffo R O. (2007a) *Nat. Mater.* 6, 997-1003.
Dalby M J, Biggs M J, Gadegaard N, Kalna G, Wilkinson C D, Curtis A S. (2007b) *J. Cell. Biochem.* 100, 326-338.
Dalby M J, Gadegaard N, Curtis A S, Oreffo R O. (2007c) *Curr. Stem Cell Res. Ther.* 2, 129-138.
Dalby M J, Gadegaard N, Tare R, Andar A, Riehle M O, Herzyk P, Wilkinson C D, Oreffo R O. (2007d) *Nat. Mater.* 6, 997-1003.
Dalby M J, Andar A, Nag A, Affrossman S, Tare R, McFarlane S, Oreffo R O. (2008) *J. R. Soc. Interface.* 5, 1055-1065.
Dalby M J. (2009) *Nanomedicine.* 4, 247-248.
Ernsting M J, Labow R S, Santerre J P. (2007) *J. Biomed. Mater. Res., Part A.* 83a, 759-769.
Extrand C W, Wright M. (2005) Microfluidic Device with Ultraphobic Surfaces. U.S. Pat. No. 6,923,216 issued Aug. 2, 2005.
Fay et al. (1991) *Biochemistry.* 30, 5066-5075.
Fonverne A, Dijon J, Ricoul F, Rouviere E. (2009) Method of manufacturing a microfluid component comprising at least one microchannel filled with nanostructures. European patent publication EP 2042467 published Apr. 1, 2009.
Griffin et al. (2003) *Febs Letters.* 546, 233-236.
Hochbaum A, Aizenberg J. (2010) *Nanoletters.* DOI: 10.1021/nl11022290k.
Jin Q, Zheng Y, Wu J, Shao J, Zhao J. (2010) Microfluidic cell array chip for high-throughput medicament screening, method and use fabricated in PDMS using modular SU-8 mold. Chinese patent publication CN 101629143 published Jan. 20, 2010.
Kimura K, Hattori A, Usui Y, Kitazawa K, Naganuma M, Kawamoto K, Teranishi S, Nomizu M, Nishida T. *Invest. Ophthalmol. Visual Sci.* 48, 1110-1118.
Krutzik et al. (2006) *Nature Methods.* 3, 361-368.
Lee L J, Yang S, Lai S, Bai Y, Huang W, Juang Y, Gregory S M. (2006) *Advances in Clinical Chemistry.* (Elsevier) pp. 255-295.
Lee L, Di Carlo D, Tanner N. (2010) Microfluidic Methods for Diagnostics and Cellular Analysis. United States patent publication US 2010/003666 published Jan. 7, 2010.
Lim C T, Zhang Y. (2007) *Biosensors and Bioelectronics.* 22, 1197-1204.
Malic L, Herrmann M, Hoa X D, Tabrizian M. (2007) *Recent Patents on Engineering.* 1, 71-88.
Marquette C, Blum L. (2006) *Biosensors and Bioelectronics.* 21, 1424-1433.
Myers F B, Lee L P. (2008) *Lab on a Chip.* 8, 2015-2031.
Nolan et al. (1998) *Nature Biotechnology.* 16, 633-638.
Regehr K J, et al. (2009) *Lab Chip.* 9, 2132-2139.
Salber J, Grater S, Harwardt M, Hofmann M, Klee D, Dujic J, Jinghuan H, Ding J, Kippenberger S, Bernd A, Groll J, Spatz J P, Moller M. (2007) *Small.* 3, 1023-1031.
Song Y. (2009) Preparation process of single nanoparticle and array-based biological molecule detector thereof) Chinese patent publication CN 101571536 published Nov. 4, 2009.
Soper S A, McCarley R L, Chen G, Shadpour H. (2008) Polymeric Nanopillars and Nanotubes, Their Manufacture and Uses. International patent publication WO 2008/097360 published Aug. 14, 2008.
Weigl B, Domingo G, LaBarre P, Gerlach J. (2008) *Lab on a Chip.* 8, 1999-2014.
Zhang Y, Ozdemir P. (2009a) *Analytica Chimica Acta.* 638, 115-125.
Zhang C, Xing D, Li Y. (2009b) *Biotechnology Advances.* 25, 483-514.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A microfluidic device comprising a monolithic polymeric substrate patterned with one or more micro-scale channels in fluid communication with one or more microfluidic chambers, a surface in the monolithic polymeric substrate comprising an ordered array of nano-scale elements suitable for plasmonic resonance reading of a fluid on the surface, the nano-scale elements having cross-sectional dimensions in a range of from 10 nm to 1000 nm, the array having a spacing distance between the elements where a cross-sectional dimension to spacing distance ratio is greater than 0.2.

2. The device according to claim 1, wherein the polymeric substrate comprises a thermoplastic polymer, a biodegradable polymer, an elastomer, polydimethylsiloxane or any blend thereof.

3. The device according to claim 1, wherein the device is a cell culture system and comprises one or more valves, conduits, inlets or outlets, wherein at least one of the ordered arrays of nano-scale elements is in at least one of the microfluidic chambers, and the nanoscale elements are patterned on microstructures to provide two levels of topographical cues.

4. The device according to claim 1, wherein the nano-scale elements comprise one or more of nanopillars, nanoposts, nanodots, nanorods, nanopyramids, nanocrescents, nanodisks, nanodomes, nanoholes, nanogratings and nanogrooves with the aspect ratio of individual nanoscale elements being in a range of from 10:1 to 1:10 and the nano-scale elements are metalized with their cross-sectional dimension to spacing distance ratio is in a range of from 0.2 to 1.5.

5. The device according to claim 1, wherein size, spacing, geometry or any combination thereof of the nano-scale elements in the ordered array have standard deviations from their respective averages of no more than 3%.

6. The device according to claim 1, wherein the cross-sectional dimension to spacing distance ratio is in a range of from 0.2 to 1.5.

7. The device according to claim 1, wherein the nano-scale elements are metalized.

8. The device according to claim 1, wherein:
the nano-scale elements are patterned on microstructures to provide two levels of topographical cues; and
an aspect ratio of individual nano-scale elements is in a range of from 10:1 to 1:10.

9. The device according to claim 1, wherein at least one ordered array of nano-scale elements is in a microfluidic chamber.

10. The device according the claim 1, wherein the monolithic polymeric substrate comprises a cycloolefin polymer, or a thermoplastic elastomer.

11. The device according the claim 1, wherein the device is a cell culture system.

12. The device according the claim 1, wherein at least part of the ordered array of nano-scale elements is in at least one of the microfluidic chambers.

13. The device according to claim 1, wherein the cross-sectional dimensions to spacing distance ratio is in a range of from 0.5 to 1.

14. The device according to claim 1, wherein the nano-scale elements comprise one of more of nanopillars, nanoposts, nanodots, nanorods, nanopyramids, nanocrescents, nanodisks, nanodomes, nanoholes, nanogratings, and nanogrooves.

15. The device according to claim 1, further comprising: one or move valves, conduits, inlets, or outlets.

16. The device according to claim 1, wherein the nano-scale elements are patterned on microstructures to provide two levels of topographical cues.

17. The device according the claim 1, wherein an aspect ratio of individual nano-scale elements is in a range of from 10:1 to 1:10.

18. A method for using the device defined in claim 1, the method comprising: loading the one of more microfluidic chambers with cells; allowing cell attachment to the one or more microfluidic chambers; and taking plasmonic resonance readings of cells.

19. The method according to claim 18, wherein one of the plasmonic resonance readings is made according to reflection-mode surface plasmon resonance, transmission-mode surface plasmon resonance, localized surface plasmon resonance or surface-enhanced Raman spectroscopy.

20. The method according to claim 18, wherein the plasmonic resonance monitors cellular behavior, motility, attachment, viability, biomolecule interactions or any combination thereof.

21. The method according to claim 18, wherein the method is for screening molecular or cellular targets, cellular identification, screening single cells for RNA or protein expression, monitoring cell response to different stimuli, genetic diagnostic screening at single cell level, or performing single cell signal transduction studies.

22. The method according the claim 18, wherein loading the cells comprises using pressure-driven flow to transport cells in suspension from a plurality of cell-loading channels to a plurality of the one or more microfluidic chambers, which are cell culture chambers.

23. The method according to claim 22, further comprising: injecting fresh media in each of the cell culture chambers via a plurality of perfusion channels, following cell attachment.

24. The method according the claim 18, further comprising: functionalizing the one of more microfluidic chambers prior to loading the cells, to monitor cell substrate interactions or for the detection of biochemical targets excreted or extracted from the cells.

* * * * *